United States Patent [19]
Chen

[11] Patent Number: 5,324,222
[45] Date of Patent: Jun. 28, 1994

[54] ULTRA-SOFT, ULTRA-ELASTIC AIRFOILS

[75] Inventor: John Y. Chen, Pacifica, Calif.

[73] Assignee: Applied Elastomerics, Inc., Pacifica, Calif.

[21] Appl. No.: 876,118

[22] Filed: Apr. 29, 1992

Related U.S. Application Data

[63] Continuation of Ser. No. 527,058, May 21, 1990, abandoned, which is a continuation-in-part of Ser. No. 211,426, Jun. 24, 1988, Pat. No. 5,153,254, which is a continuation-in-part of Ser. No. 921,752, Oct. 21, 1986, abandoned, which is a continuation-in-part of Ser. No. 572,172, Jan. 18, 1984, Pat. No. 4,618,213, which is a continuation-in-part of Ser. No. 458,703, Jan. 17, 1983, abandoned, which is a continuation-in-part of Ser. No. 134,977, Mar. 28, 1980, Pat. No. 4,369,284, which is a continuation-in-part of Ser. No. 916,731, Jun. 19, 1978, abandoned, which is a continuation-in-part of Ser. No. 815,315, Jul. 13, 1977, abandoned, which is a continuation-in-part of Ser. No. 778,343, Mar. 17, 1977, abandoned.

[51] Int. Cl.$^5$ .............. A63H 27/00; A63H 27/14; A63H 27/18; A63H 3/00
[52] U.S. Cl. ........................ 446/34; 446/46; 446/48; 446/61; 446/62; 446/66
[58] Field of Search ............ 446/34, 46, 48, 61, 446/62, 66

[56] References Cited

U.S. PATENT DOCUMENTS

| | | | |
|---|---|---|---|
| 2,454,598 | 11/1948 | Doyle | 446/66 |
| 3,653,151 | 4/1972 | Laurent | 446/66 |
| 3,676,387 | 7/1972 | Lindlof | 260/28.5 B |
| 4,104,822 | 10/1976 | Rodgers | 446/48 |
| 4,369,284 | 6/1983 | Chen | 524/476 |
| 4,466,212 | 8/1984 | Lehman | 446/46 |
| 4,516,947 | 5/1985 | Pircher | 446/46 |
| 4,516,996 | 5/1985 | Rodarte | 446/46 |
| 4,560,358 | 12/1985 | Adler | 446/46 |
| 4,618,213 | 10/1986 | Chen | 446/486 X |
| 4,669,995 | 6/1987 | Lombard | 446/48 |
| 4,669,996 | 6/1987 | Bershak | 446/48 |
| 4,681,553 | 7/1987 | Rodarte | 446/46 |
| 4,737,128 | 4/1988 | Moormann et al. | 446/46 |
| 4,820,230 | 4/1989 | Richards | 446/48 |
| 4,940,441 | 7/1990 | Novinsky | 446/46 |
| 4,944,363 | 7/1990 | Osher | 273/58 |
| 4,944,707 | 7/1990 | Silverglate | 496/48 |
| 4,957,465 | 9/1990 | Madhava | 446/66 |
| 5,026,054 | 6/1991 | Osher et al. | 446/46 |

FOREIGN PATENT DOCUMENTS

| | | | |
|---|---|---|---|
| 223983 | 10/1962 | Austria | 446/61 |
| 1268431 | 1/1969 | United Kingdom . | |
| 2021960 | 12/1979 | United Kingdom | 446/61 |

OTHER PUBLICATIONS

Brochure "Pelaspan Expandable Polystyrene" Catalog 171-90 Dow Chem Co. Feb. 1958.

*Primary Examiner*—Herbert J. Lilling

[57] ABSTRACT

A novel rotating aerodynamic toy comprising a ultra-elastic gel airfoil which is suitable for launch in light or heavy wind conditions and capable of performing various aerodynamic effects including climb, stall, return, straight-line flight and other aerobatics. The ultra-elastic properties of the airfoil allow the airfoil to transform its aerodynamic profile at launch and while in flight.

20 Claims, 4 Drawing Sheets

Characteristic Flight Regions for Different Wind Speeds

ULTRA-SOFT, ULTRA-ELASTIC AIRFOILS

RELATED APPLICATIONS AND PATENTS

This is a continuation of copending application Ser. No. 07/527,058 filed on May 21, 1990, now abandoned, which is a continuation-in-part of copending application Ser. No. 211,426 filed Jun. 24, 1988 (now issued as U.S. Pat. No. 5,153,254 on Oct. 6, 1992) which is a continuation-in-part of copending application Ser. No. 921,752 filed Oct. 21, 1986, now abandoned, which is a continuation-in-part of application Ser. No. 572,172, filed 18 Jan. 1984 and issued as U.S. Pat. No. 4,618,213 on 21 Oct. 1986, which is a continuation-in-part of application Ser. No. 458,703, now abandoned filed 17 Jan. 1983, which is a continuation-in-part of application Ser. No. 134,977, filed 28 Mar. 1980 and issued as U.S. Pat. No. 4,369,284 on 18 Jan. 1983, which in turn is a continuation-in-part of application Ser. No. 916,731, filed 19 Jun. 1978, now abandoned which is a continuation-in-part of application Ser. No. 815,315, filed 13 Jul. 1977, now abandoned which is a continuation-in-part of application Ser. No. 778,343, filed 17 Mar. 1977, now abandoned. The subject matter contained in the related applications and patents are specifically incorporated herein by reference.

FIELD OF THE INVENTION

The present invention relates to aerodynamic toys.

BACKGROUND OF THE INVENTION

There are various prior art aerodynamic toys (flyers) in the form of airfoils. The ability to safely launch and land such flyers is of major concern for everyone involved with safety. Flyers of rigid construction have been fitted with rubber bumpers. While some flyers are completely made of soft foam or sheet rubber. Others are inflatable or, in some instants, are substantially made of fabric.

In general, prior art flyers are designed to maintain a rigid or fixed configuration or shape (i.e. aerodynamic profile) during flight. The typical pocket flyers (i.e. made from fabric or rubber) are somewhat flexible and are much safer; they are also foldable. In flight, however, due to the rotation imparted to the flyer at launch (i.e. centrifugal force), these more flexible flyers also exhibit a substantially rigid or fixed aerodynamic profile characterized by a substantially fixed radii or shape.

The inflatable flyers of the prior art are designed with shape holding features which serve to maintain a predetermined or preselected aerodynamic profile. The rigid, fixed, build-in aerodynamic profiles which are characteristic of all prior art flyers determine the toy's ultimate aerodynamic characteristics and most importantly, their lift/drag characteristics. These flyers of the prior art (when launched) will substantially fly in a predetermined flight-path and at all times, subject to the mercy of the wind.

Most importantly, all prior art flyers are not well suited for flying in the wind. It is well known that the wind is not especially kind to such flyers and throwers must avoid anything more than a very light breeze. As a rule, if there is more than 2-5 mph of wind, it's too windy to safely throw any prior art flyer; it will simply be blown away in anything more than a very light breeze. Even the most advanced, high-tech flyer, if caught by a light wind, can become unpredictable!

SUMMARY OF THE INVENTION

I have unexpectedly discovered novel airfoils made from ultra-soft, ultra-elastic materials, such as gels, which are capable of sustained flight and performing various aerodynamic effects such as climb, stall, return, and other flight aerobatics. The airfoils of the invention can be launched and flown safely under extremely varying wind conditions of less than 0.5 mph to greater than 40 mph. The high Reynolds Number (flight performance) characteristics of the airfoils are attributed to their ultra-elastic properties which allows the (deformable) airfoils to transform its aerodynamic profile at launch and during flight.

The various aspects and advantages of the invention will become apparent to those skilled in the art upon consideration of the accompanying disclosure and the drawings.

DETAILED DESCRIPTION OF THE INVENTION

It is somewhat strange and wonderful to watch an airfoil of the invention (thrown into a moderate wind) take off and soar like an "eagle" to an incredible height, stall, then drive earthward like an eagle when attacking prey from above. It is even more strange to catch an airfoil of the invention! As it hits the palm of the hand, the impact gives the feeling of catching a small anesthetized Amazon frog falling from the sky!

The airfoils of the present invention are not limited to any particular aerodynamic profile, although certain profiles may have advantages over others such as for speed, distance, climb, stall, return, etc. The basic principles of aerodynamics and airfoil design can be utilized to assist in selecting and forming the shapes and profiles of the ultra-soft, ultra-elastic gel airfoils of the invention. For example, see *Shape and Flow*, by A. H. Shapiro, 1961, Doubleday & Company, Inc.; *Aerodynamics of Wings and Bodies*, by H. Ashley, at al, 1965, Dover Publications, Inc.; *Theory of Flight*, by R. Von Mises, 1959, Dover Publications, Inc.; *Aerodynamics Theory*, W. F. Durand, Editor, Volume I-VI, 1963, Peter Smith Publisher, Inc.; *Rotary-Wing Aerodynamics*, W. Z. Stepniewski, et al, Volume I & II, 1984, Dover Publications, Inc.; *Incompressible Aerodynamics*, B. Thwaites, Editor, 1960, Oxford Press; *Modern Developments in Fluid Dynamics*, S. Goldstein, Editor, Volume I & II, 1950, Oxford Press; *Hydrodynamics*, by Sir H. Lamb, 1945, Dover Publications, Inc.; *Fluid-Dynamic Lift*, by S. F. Hoerner, 1975, Published by Mrs. Liselotte A. Hoerner; and *Fluid-Dynamic Drag*, by S. F. Hoerner, 1958, Published by the Author; *Foundations of Aerodynamics*, by Kuethe, Arnold M., et al, 3rd Edition, John Wiley & Sons, 1976. The subject matter contained in these publications are specifically incorporated herein by reference.

Generally, any aerodynamic profile can be selected for use in the design of the airfoil of the invention provided the profile selected gives the airfoil (when launched by hand) a sustained flight-time in air that is greater than the time required for the airfoil to fall the vertical distance to the ground in free-fall when released from the same launch height.

Figure 1:
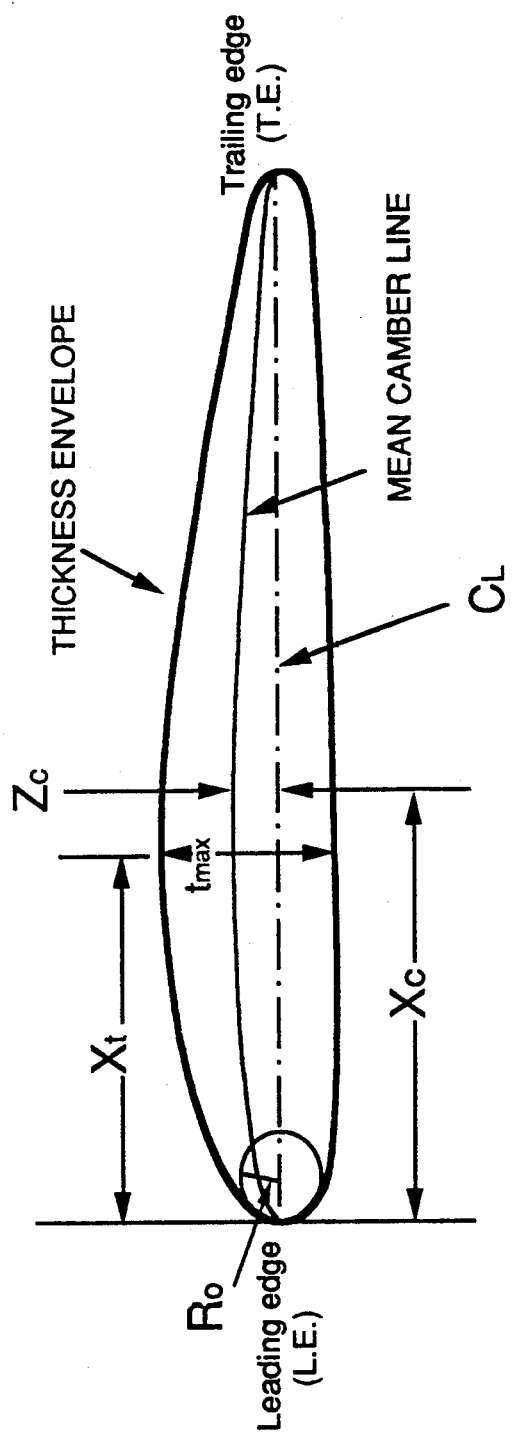
FIG. 1. Side view of an elongated airfoil of the invention showing various geometrical variables of a profile cross section.

The airfoils of the invention comprises a thickness envelope wrapped around a mean camber line as shown in FIG. 1.

Figure 2:
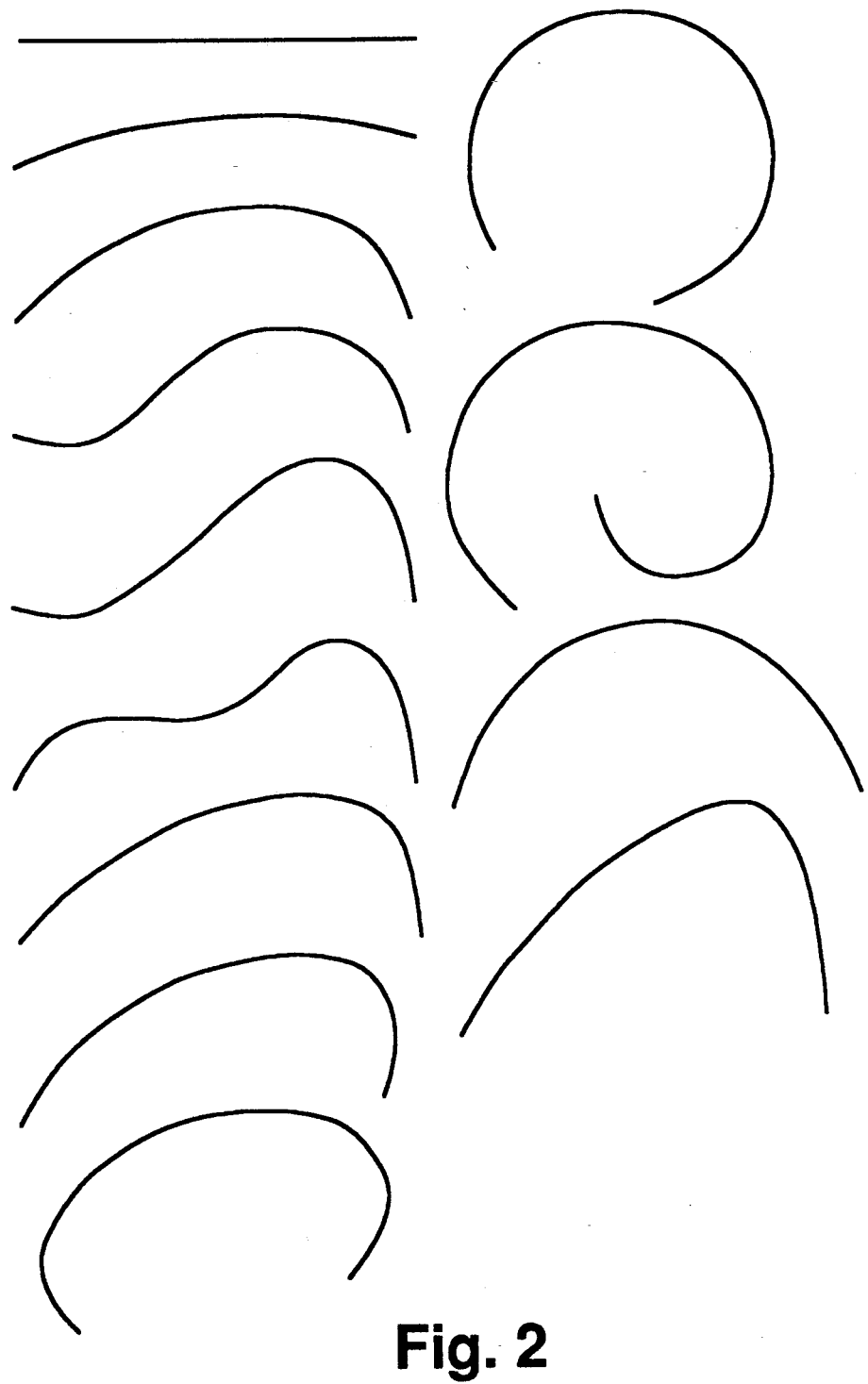
FIG. 2. Side view of selected examples of mean camber lines of airfoils of the invention.
Figure 3:
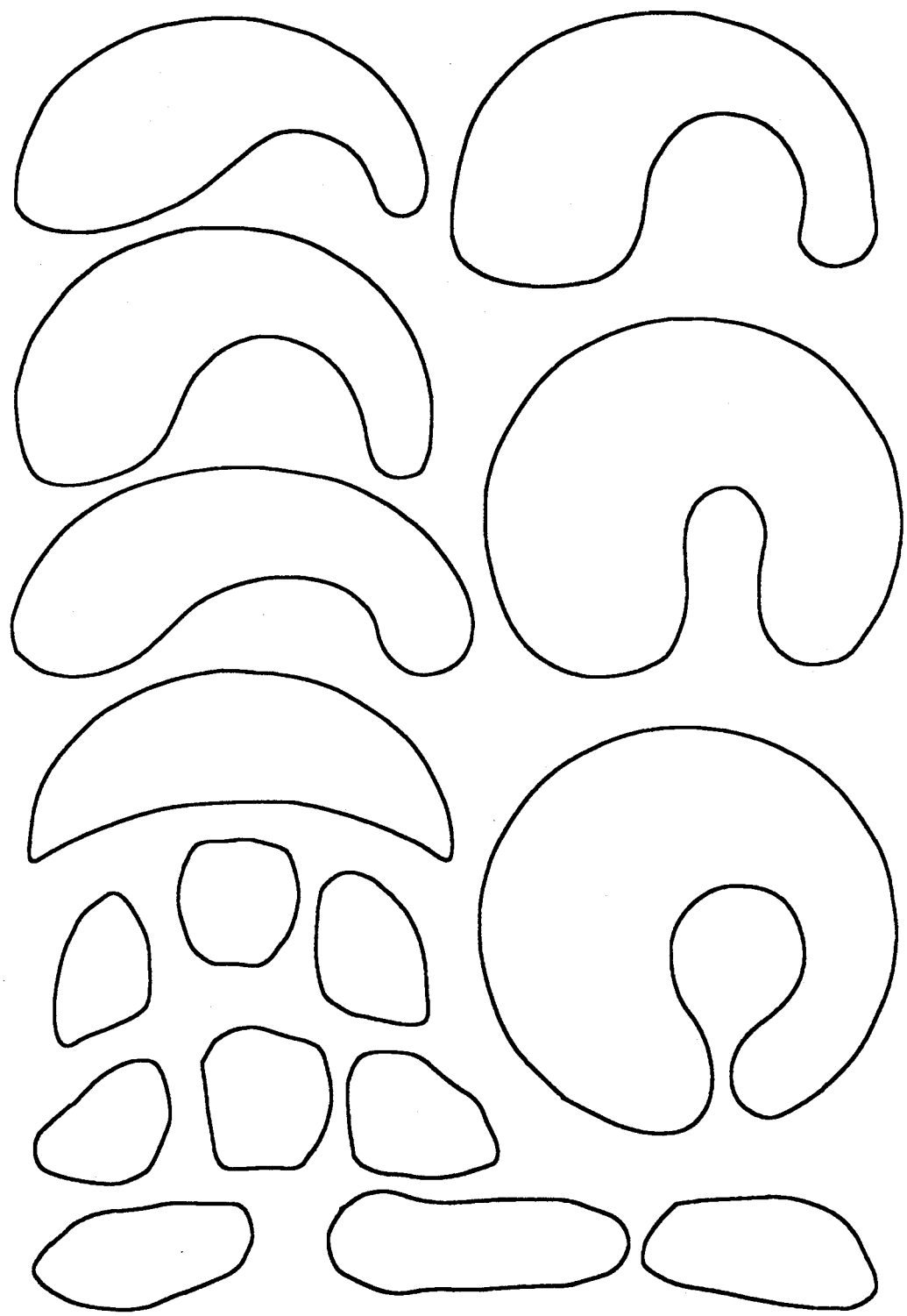
FIG. 3. Side view of various profile cross sections of elongated and non-elongated airfoils.

Aerodynamic profiles for the airfoil of the invention can be selected with mean camber lines shown in FIG. 2 or any intermediate mean camber line. The mean camber line lies halfway between the upper and lower surfaces of the airfoil and intersects the chord line at the leading and trailing edges. An intermediate mean camber line can be obtained from any two adjacent mean camber lines shown in FIG. 2 by the drawing a new intermediate mean camber line halfway between the adjacent mean camber lines. Likewise an intermediate mean camber line can be used together with another mean camber line or another intermediate mean camber line to derive a new intermediate mean camber line. The thickness envelope (bounded by an upper surface and a lower surface) of the airfoils of the invention can be of any suitable thickness provided the resulting airfoil is capable of sustained flight. Other geometrical variables of airfoils of the invention are shown in FIG. 1; they include the cord line or curve $C_L$; the maximum camber $Z_c$ of the mean camber line or curve and its distance $X_c$ behind the leading edge; the maximum thickness $t_{max}$ and its distance $x_t$ behind the leading edge; the radius of curvature of the surface at the leading edge, $r_o$, and the angle between the upper and lower surfaces at the trailing edge. In the design of the airfoils of the invention, the geometrical variables should be selected so as to provide the instant airfoils with the ability for sustained flight in low as well as high wind conditions.

A suitable range for $C_L$ is less than about 3 cm to about 30 cm or more. The value $(X_c - X_t) = C_o$ can range from less than about 2 cm to greater than about 20 cm. The variable $t_{max}$ can range from less than about 1 cm to greater than about 7 cm.

The aerodynamic profile (i.e. cross-sectional geometry) of the airfoils of the invention can be varied as desired. A helpful way of designing and/or viewing the airfoils' profile from the side is to vertically cut the airfoils into adjacent slices. For example, the adjacent slices can be a series of different cross sections (i.e. cross sections of different geometrical variable values). The airfoils of the invention can be designed with any desired profile cross section or varying profile cross sections provided such profiles will maintain sustained flight.

Since the instant airfoils are three dimensional objects, they can be sliced to show more than one cross section. For example, viewing down on the upper surface, airfoils of the invention can have shapes such as a ring, circle, square, triangle, parallelogram, rhombus, trapezoid, quadrilateral, pentagon, hexagon, heptagon, octagon, nonagon, decagon, undecagon, dodecagon, polygon, sector, a circle, an ellipse, a parabola and the like. The general solid shape of the instant airfoils can be a hemisphere, spherical triangle, spherical segment, curved volume of a right cylinder, curved volume of a right cone, oblate hemispheroid, semi-hemispheroid, quai-hemnispheriod, prolate hemispheroid and the like. Other unusual solid shapes can include a hemi-egg shape, hemi-papaya shape, hemi-pear shape or almost any hemi-fruit shape. Still other shapes can include hemi-American-football shape.

The upper surface of airfoils of the invention can be smooth, patterned, rough, and the like. The upper surface can also contain one or more cavities, slots or holes completely through the airfoil. The lower surface can be curved to any desired degree (centered or off-centered), or it can contain one or more cavities (centered or off-centered) of any desired shape.

The airfoils of the invention can be launched by hand. Launching aids can also be used to grip the trailing edge of the airfoils such as a "V" shaped device to simulate the fingers and thumb. Normally, an airfoil of the invention is launched with a spin by the wrist. The spinning wrist action impacts rotation to the airfoil so as to elongate the airfoil as it leaves the hand. The elongated airfoil will continue to spin and maintain its flight path while at the same time reach a maximum elongation because of centrifugal force and then retract back to its original shape as the spin slows to a stop.

Elongations of the airfoils (as measured from leading edge to trailing edge) under flight conditions can reach 50% or more. Elongations of 100%, 200%, 300%, 400%, 500%, 600%, 700% and higher are possible under flight conditions. Airfoils of of the invention can be designed to withstand elongations higher than 1,000% which can occur at extreme high spin speeds.

Airfoils of the invention can fly at rotational speeds, $R_s$, of less than about 20 rpm to greater than about 1,500 rpm.

The instant airfoils can be launched at speeds, $S_1$, less than about 5 mph to about 80 mph and higher.

Airfoils were tested in the laboratory and in the field using a few simple equipment. Airfoils were mounted on a variable spinning device. The rotational speeds were measured by using a GenRad 1546 digital stroboscope. Both natural and laboratory winds were measured using a Hall Airspeed Indicator. Laboratory winds (up to 55 mph) were generated using a Rotron Inc. Centrimax ® model CXH33 Blower and wind tunnel assembly. Airfoil characteristics such as: angle of attack, geometrical profile, climb, drag, lift, Reynolds number, stall, rotational velocity, aspect ratio, stall, twist, pitch, sideslip angle, cord length, yaw angle, deformations, vibrations, air circulation and the like can be observed, measured and/or calculated under a variety of flight conditions.

Two Reynolds Numbers can be used to characterize the airfoils of the invention. These are: $R_{e1}$ and $R_{e2}$.

$$R_{e1} = \{[S_1 - R_s(C_L/2)]C_o\}/V_{u,r}$$

and $$R_{e2} = \{[S_1 + R_s(C_L/2)]C_o\}/V_{u,r}$$

where $V_{u,r}$ = Viscosity/Density or approximate = 0.15 cm$^2$/second in air. $R_{e1}$ and d $R_{e2}$ can range from less than about 200 to about 100,000 or more. More suitably, $R_{e1}$, and $R_{e2}$ can range from less than about 5000 to about 50,000 and higher.

The instant airfoils can fly under almost any wind condition, almost no wind (0.001 m.p.h.), low wind (0.5 m.p.h.), light wind (0.6 m.p.h.), moderate light wind (15 m.p.h.), moderate wind (25 m.p.h.), high wind (35 m.p.h.) and even under wind gust conditions greater than 40 m.p.h.

The instant airfoils can be made from any gel material with suitable elastic properties. Gels described in patents and applications under "RELATED APPLICATIONS AND PATENTS", now sold under trademark Memory-Gel ®, are especially suitable for forming the airfoils of the invention. Gels less suitable for use include polymer gels, crosslinked polymer gels, and the like. These are found in U.S. Pat. Nos. 4,833,193; 4,709,982; 4,716,183; 4,497,538; 4,509,821; 4,351,913 and 4,432,607. Other less suitable gels include high strength silicone gels, urethane gels, water gels, and the like.

Gels especially suitable for use in making airfoils of the invention can be prepared by melt blending an admixture consisting essentially of:

(A) 100 parts by weight of a high viscosity triblock copolymer of the general configuration poly(styrene-ethylene-butylene-styrene) wherein said styrene end block to ethylene and butylene center block ratio is about 31:69 to about 40:60;

(B) from about 300 to about 1,600 parts by weight of an plasticizing oil.

Examples of triblock copolymers that can be utilized to achieve one or more of the novel properties necessary for airfoils of the present invention are styrene-ethylene-butylene-styrene block copolymers (SEBS) available from Shell Chemical Company and Pecten Chemical Company (divisions of Shell Oil Company) under trade designations Kraton G 1651, Kraton G 4600, and Kraton G 4609. Other less suitable (SEBS) polymers are Tuftec H 1051, H1041, H1052 and the like made by Asahi Chemical. These polymers can be combined with Kraton G as desired.

Minor amounts of other polymers and copolymers can be melt blended with the styrene-ethylene-butylene-styrene block copolymers mentioned above without substantially decreasing the desired properties. Such polymers may include (SBS) styrene-butadiene-styrene block copolymers, (SIS) styrene-isoprene-styrene block copolymers, (low styrene content SEBS) styrene-ethylene-butylene-styrene block copolymers, (SEP) styrene-ethylene-propylene block copolymers $(SB)_n$ styrene-butadiene and $(SEB)_n$, $(SEBS)_n$, $(SEP)_n$, $(SI)_n$ styrene-isoprene multiarm, branched, and star shaped copolymers and the like. Still, other homopolymers can be utilized in minor amounts; these include: polystyrene, polybutylene, polyethylene, and the like.

The proportion of hydrocarbon plasticizing oil in (B) is more preferably from about 350 to about 1,600 parts per 100 parts of the triblock copolymer.

The major triblock copolymers employed in the present invention have the more general configuration A-B-A wherein each A is a crystalline polymer end block segment of polystyrene; and B is a elastomeric polymer center block segment of poly(ethylene-butylene). The poly(ethylene-butylene) and polystyrene portions are incompatible and form a two-phase system consisting of sub-micron domains of glassy polystyrene interconnected by flexible poly(ethylene-butylene) chains. These domains serve to crosslink and reinforce the structure. This physical elastomeric network structure is reversible, and heating the polymer above the softening point of polystyrene temporarily disrupt the structure, which can be restored by lowering the temperature. Most recent reviews of triblock copolymers are found in the "ENCYCLOPEDIA OF POLYMER SCIENCE AND ENGINEERING", Volume 2 and 5, 1987-1988; "Thermoplastic elastomers", MODERN PLASTICS ENCYCLOPEDIA, 1989; and Walker, B. M., Ed., et al., HANDBOOK OF THERMOPLASTIC ELASTOMERS, Van Nostrand Reinhold Co., 2nd Edition, 1988. (incorporated herein by reference).

Plasticizers particularly preferred for use in practicing the present invention are will known in the art, they include rubber processing oils such as paraffinic and naphthenic petroleum oils, highly refined aromatic-free paraffinic and naphthenic food and technical grade white petroleum mineral oils, and synthetic liquid oligomers of polybutene, polypropene, polyterpene, etc. The synthetic series process oils are high viscosity oligomers which are permanently fluid liquid nonolefins, isoparaffins or paraffins of moderate to high molecular weight. Many such oils are known and commercially available.

The triblock copolymer component by itself lacks the desired properties; whereas, when the triblock copolymer is combined with selected plasticizing oils with an average molecular weight preferably of about 200 to about 800 or more, as determined by ebulliscopic methods, wherein, for most purposes, the oil constitutes about 300 to about 1,600 parts and more preferably about 350 to about 1,600 parts by weight of the triblock copolymer, that an extremely soft and highly elastic material is obtained. This transformation of the triblock copolymer structure in heated oil resulting in a composition having a gel rigidity preferably of about 20 gram to about 800 gram Bloom or more and substantially without oil breedout along with high tensile strength and elongation and other desirable combination of physical properties is unexpected. As used herein, the term "gel rigidity" in gram Bloom is determined by the gram weight required to depress a gel a distance of 4 mm with a piston having a cross-sectional area of 1 square centimeter at 23° C.

In accordance with the practice of the present invention, the aforementioned molecular weight range plasticizing oils are most preferred. Generally, plasticizing oils with average molecular weights less than about 200 and greater than about 700 may also be used.

The composition of this invention can also contain useful amounts of conventionally employed additives such as stabilizers, antioxidants, antiblocking agents, colorants, fragrances, flame retardants, and the like to an extend not affecting or substantially decreasing the desired properties of the present invention.

Additives useful in the composition of the present invention include: tetrakis[methylene 3,-(3'5'-di-tertbutyl-4''-hydroxyphenyl)propionate]methane, octadecyl 3-(3'',5''-di-tert-butyl-4''-hydroxyphenyl)propionate, distearyl-pentaerythritol-diproprionate, thiodiethylene bis-(3,5-ter-butyl-4-hydroxy)hydrocinnamate, (1,3,5-trimethyl-2,4,6-tri[3,5-di-tert-butyl-4-hydroxybenzyl]-benzene), 4,4''-methylenebis(2,6-di-tert-butylphenol), steraric acid, oleic acid, stearamide, behenamide, oleamide, erucamide, N,N''-ethylenebisstearamide, N,N''-ethylenebisoleamide, sterryl erucamide, erucyl erucamide, oleyl palmitamide, stearyl stearamide, erucyl stearamide, metallic pigments (aluminum and brass flakes), $TiO_2$, mica, fluorescent dyes and pigments, phosphorescent pigments, aluminatrihydrate, antimony oxide, iron oxides ($Fe_3O_4$, —$Fe_2O_3$, etc.), iron cobalt oxides, chromium dioxide, iron, barium ferrite, strontium ferrite and other magnetic particle materials, molybdenum, silicone fluids, lake pigments, aluminates, ceramic pigments, ironblues, ultramarines, phthalocynines, azo pigments, carbon blacks, silicon dioxide, silica, clay, feldspar, glass microspheres, barium ferrite, wollastonite, talcum, and the like. The report of the committee on *Magnetic Materials*, Publication NMAB-426, National Academy Press (1985) is incorporated herein by reference.

The compositions of the present invention are prepared by blending together the components including other additives as desired at about 23° C. to about 100° C. forming a paste like mixture and further heating said mixture uniformly to about 150° C. to about 200° C. until a homogeneous molten blend is obtained. These components blend easily in the melt and a heated vessel equipped with a stirrer is all that is required.

The composition of the airfoils of the invention is excellent for cast molding and the molded products have various excellent characteristics which cannot be anticipated form the properties of the raw components.

The basis of this invention resides in the fact that a high viscosity poly(styrene-ethylene-butylene-styrene) triblock copolymer when blended in the melt with an appropriate amount of plasticizing oil makes possible the attainment of compositions having a desirable combination of physical and mechanical properties, notably high elongation at break of at least 1,600%, ultimate tensile strength of about at least $8 \times 10^5$ dyne/cm$^2$, low elongation set at break of substantially not greater than about 2%, tear resistance of at least $5 \times 10^5$ dyne/cm$^2$, substantially about 100% snap back when extended to 1,200% elongation, and a gel rigidity of substantially not greater than about 800 gram Bloom.

More specifically, the composition utilized in the present invention exhibit one or more of the following properties. These are: (1) tensile strength of about $8 \times 10^5$ dyne/cm$^2$ to about $10^7$ dyne/cm$^2$; (2) elongation of about 1,600% to about 3,000% and higher; (3) elasticity modulus of about $10^4$ dyne/cm$^2$ to about $10^6$ dyne/cm$^2$; (4) shear modulus of about $10^4$ dyne/cm$^2$ to about $10^6$ dyne/cm$^2$ as measured with a 1, 2, and 3 kilogram load at 23° C.; (5) gel rigidity of about 20 gram Bloom or lower to about 700 gram Bloom as measured by the gram weight required to depress a gel a distance of 4 mm with a piston having a cross-sectional area of 1 square cm at 23° C.; (6) tear propagation resistance of at least about $5 \times 10^5$ dyne/cm$^2$; (7) and substantially 100% snap back recovery when extended at a crosshead separation speed of 25 cm/minute to 1,200% at 23° C. Properties (1), (2), (3), and (6) above are measured at a crosshead separation speed of 25 cm/minute at 23° C.

The instant airfoils molded from the compositions have various additional important advantages in that they do not crack, creep, tear, crack, or rupture in flextural, tension, compression, or other deforming conditions of normal use; but rather the molded airfoils made from the instant composition possess the intrinsic properties of elastic memory enabling the airfoils to recover and retain its original molded shape after many extreme deformation cycles. In applications where low rigidity, high elongation, good compression set and excellent tensile strength are important, the instant compositions would be preferred.

The composition can also be formed into shapes for use as optical lenses. The optical lenses may have two or more opposite regular surfaces either both curved or one curved and the other plane. Such lenses may be used either singly or combined in an optical instrument or in the hand for forming an image by focusing rays of light. Example of lens shapes include plano-convex, bi-convex converging meniscus, plano-concave, bi-concave, diverging meniscous, cylindrical, and spherical.

The composition of the invention is extremely versatile; it can be casted, molded, or extruded to make the airfoils of the invention.

The invention is further illustrated by means of the following illustrative embodiments, which are given for purpose of illustration only and are not meant to limit the invention to the particular components and amounts disclosed.

EXAMPLE I

One hundred parts by weight of a high viscosity poly(styrene-ethylene-butylene-styrene) triblock copolymer (Shell Kraton G 1651) having a styrene end block to ethylene and butylene center block ratio of about 33:67 with 0.1 parts by weight of a stabilizer (Irrganox 1010) was melt blended with various quantities of a naphthenic oil (ARCO Tufflo 6024). Samples having the dimensions of 5 cm $\times$ 5 cm $\times$ 3 cm were cut and measured for gel rigidity on a modified Bloom gelometer as determined by the gram weight required to depress the gel a distance of 4 mm with a piston having a cross-sectional area of 1 cm$^2$. The average gel rigidity values with respect to various oil concentrations are set forth in Table I below.

TABLE I

| Oil per 100 parts of Triblock copolymer | Gel Rigidity, gram Bloom |
| --- | --- |
| 360 | 500 |
| 463 | 348 |
| 520 | 280 |
| 615 | 240 |
| 635 | 220 |
| 710 | 172 |
| 838 | 135 |
| 1,587 | 54 |

TABLE II

| Experiment | 400% elongation Rotation Speed rpm | Gel Rigidity, gram Bloom |
| --- | --- | --- |
| 1 | 732 | 51 |
| 2 | 805 | 75 |
| 3 | 929 | 105 |
| 4 | 941 | 109 |
| 5 | 835 | 825 |
| 6 | 989 | 113 |
| 7 | 1095 | 140 |

EXAMPLE II

Two plano-convex lenses having a rigidity of 105 are joined at their bases to form a sphere. The resultant sphere is thrown against a hard smooth glass door and upon impact is deformed into the shape of a pancake; upon recovery back to the original shape of a sphere, it slowly roll down the surface of the door under the force of gravity. The lenses are then joined at their base with only half of the total base surface areas overlapping; the joined lenses are thrown against a hard smooth glass door and upon recovery the lenses in union rolls down the surface of the door showing cam rolling action.

Such a plano-convex lens can serve as a symmetrical airfoil provided it is detackified with talcum or other detackfying agents. Otherwise if thrown in its tacky state, chances are it will hit your foot. A stretchey, gooey, soft and sticky toy in the shape of a plano-convex lens (trademarked Glueball ®) has been marketed since 1983 by Applied Elastomerics, Inc. As one writer have said of this toy and other toys like it:

"People have been known to stand in front of a large wall, and from arm's length, rear back, let fly, and miss entirely. The wall."

Although it works as an airfoil, a slight difficulty with using one-half of a detackfied Glueball ® or plano-convex lens without its lower surface curved to any degree is that it will require a much higher spin when launching such an airfoil in order to obtain the desired flight performance. The higher spin means a greater centrifugal force is needed which results often times in tearing of the underside of the airfoil only after a few throws. Moreover, the greater spin required to launch the airfoil is beyond the normal endurance of the average adult human hand and wrist.

The discovery of the present invention was made by a slight chance (funny) accident. In 1987, while examining a newly made Glueball ®, the inventor inadvertently dropped one of the hemisphere on some small pumice rocks near his foot and on picking it up, several small rocks were tenaciously attached to the hemisphere. The rocks attached to the hemisphere would not come off not matter how hard the hemisphere was shooked. The inventor next tried to sling the rocks off; it also did not work. An attempt to sling the hemisphere as hard as possible resulted in breaking a small piece of the hemisphere off thereby unintentionally releasing the hemisphere-rocks spinning into the air. The inventor observed that all the rocks separated upon release; but the hemisphere spinning with the curved side facing down did not follow the normal path of a falling projectile. Rather, it dipped drastically in midcourse and plunged into the ground picking up a hand-full of more pumice rocks. Talcum was applied to the other hemisphere; upon launched in the same manner with its curved side up, the spinning hemisphere took on a noticeably deformed shape and lifted-up into the air, maintaining a sustained flight for quite some distance. Since that day, the inventor has worked to improve on the hemisphere airfoil to solve the problem of tearing and decreasing the spin required for use by small and younger hands. Table II gives results of spin speed (rpm) as a function rigidity at an observed elongation of approximate 400%.

EXAMPLE III

Airfoil designs which require support and/or stability on its upper or lower surfaces can be made by interlocking the gel with a foam. Such a foam is SCOTFOAM ® 1/32" to ⅛" thick sheet material with 5, 10, 15, 20, 25, 30, 35, 40, 45, 50, 60, 70, 80, 90, 100, and 200 ppi.

While preferred components and formulation ranges have been disclosed herein. Persons of skill in the art can extend these ranges using appropriate material according to the principles discussed herein. Furthermore, other ways of making airfoils, such as forming a relatively low modulus inner layer followed by a high modulus outer layer, are possible, as is the use of triple-layers, etc. For example, the inner core of the airfoil can be made of urethane gel, the middle layer of silicone gel, and the outer layer of (SEBS) gel. All such variations and deviations which rely on the teachings through which the present invention has advanced the air are considered to be within the spirit and scope of the present invention.

What I claim is:

1. An aerodynamic toy comprising a camber defined by a profile in the shape of an airfoil made from an ultra-elastic gel.

2. An aerodynamic toy comprising an ultra-elastic gel in the shape of an airfoil, said airfoil having an upper surface and an lower surface defining a camber.

Figure 4:
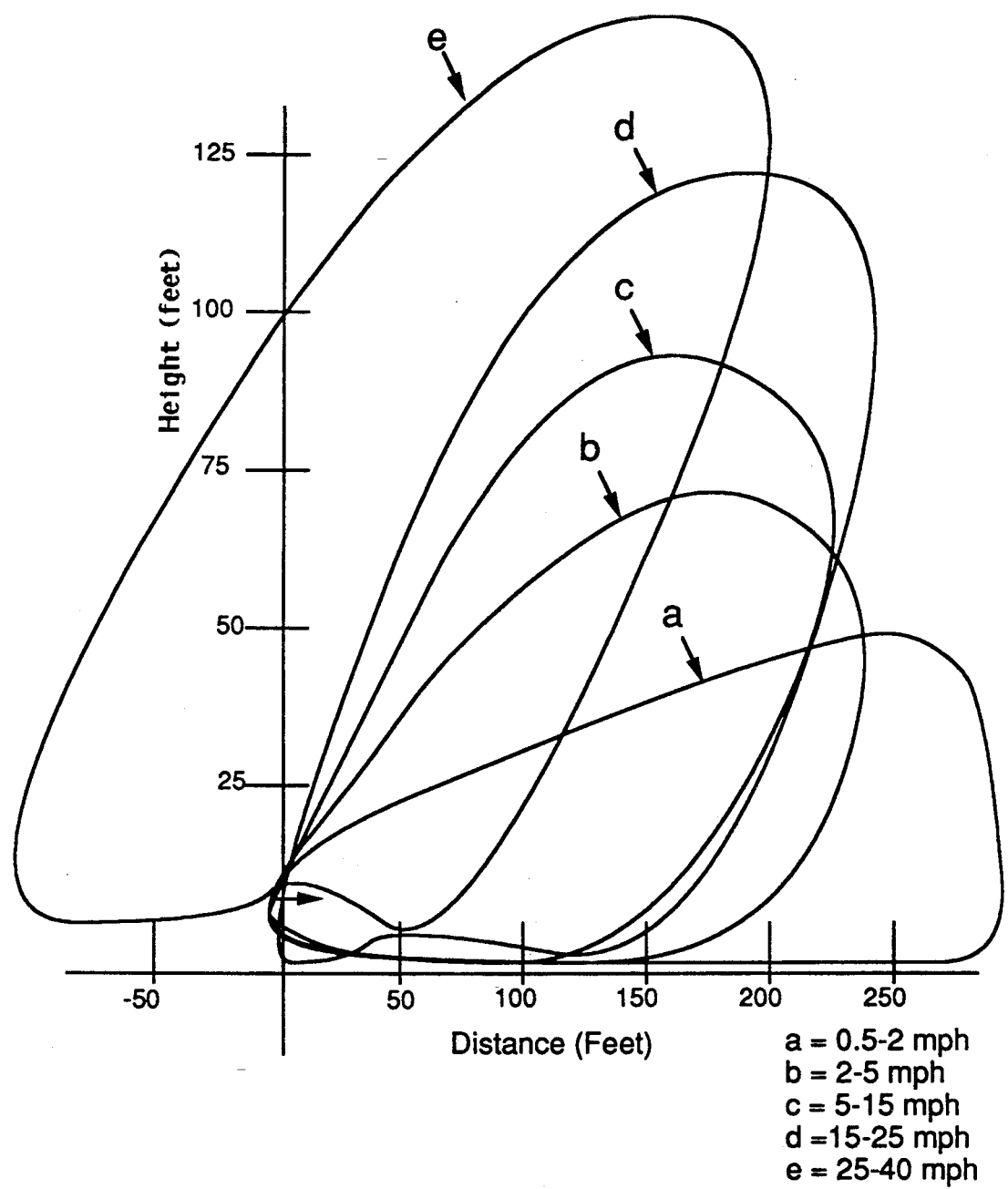
FIG. 4. Characteristic flight regions of airfoils under various wind conditions.

3. An aerodynamic toy comprising an ultra-elastic gel in the shape of an airfoil defining a camber, said airfoil capable of sustained flight in flight regions a, b, c, d, or e of FIG. 4.

4. An aerodynamic toy comprising an ultra-elastic gel in the shape of an airfoil; said airfoil having an upper surface and a lower surface defining a camber; and said gel formed from a high viscosity triblock copolymer of poly(styrene-ethylene-butylene-styrene) and a plasticizer.

5. An aerodynamic toy comprising one or more ultra-elastic gels in the shape of an airfoil; said airfoil having an upper surface and a lower surface defining a camber; at least one of said upper and lower surfaces being formed from a gel of 100 parts by weight of a high viscosity triblock copolymer of the general configuration poly(styrene-ethylene-butylene-styrene) and about 300 to about 1,600 parts by weight of a plasticizer.

6. An aerodynamic toy comprising an ultra-elastic gel in the shape of an airfoil, said airfoil having an upper surface and a lower surface defining a camber, said airfoil is made from a gel of 100 parts by weight of a high viscosity triblock copolymer of the general configuration poly(styrene-ethylene-butylene-styrene) and at least about 300 parts by weight of a plasticizer or additionally, in combination with at least one or more homopolymers or copolymers of poly(styrene-butadiene-styrene), poly(styrene-butadiene), poly(styrene-isoprene-styrene), poly(styrene-isoprene), poly(styrene-ethylene-propylene), poly(styrene-ethylene-butylene-styrene), poly(styrene-ethylene-butylene), polystyrene, polybutylene or polyethylene, wherein said copolymer is a linear, branched, multiarm, or star shaped copolymer, and wherein the said rigidity gel is about 20 gram to about 800 gram Bloom.

7. An aerodynamic toy comprising a camber defined by a profile in the shape of an airfoil made from a low rigidity gel having a gel rigidity of about 20 gram to about 800 gram Bloom.

8. An aerodynamic toy comprising an ultra-elastic gel in the shape of an airfoil, said airfoil made from a low rigidity gel having a gel rigidity of at about 20 gram to about 800 gram Bloom, said airfoil having an upper surface and an lower surface defining a camber.

9. An aerodynamic toy of claim 8, wherein said upper surface or said lower surface of said gel airfoil is interlocked with a foam material.

10. An aerodynamic toy of claim 1, 2, 3, 4 or 5, wherein said airfoil is characterized by a Reynolds Number of about 200 to about 100,000.

11. An aerodynamic toy of claim 2, 3, 4 or 5, wherein said upper surface or said lower surface of said gel airfoil is interlocked with a foam material.

12. An aerodynamic toy of claim 8, wherein said airfoil having one or more holes forming a communicating surface between said upper surface and said lower surface.

13. An aerodynamic toy of claim 1, 2, 3, 4 or 5, wherein said airfoil having a cord line length of about 3 cm to about 30 cm measured at an elongation of at least 50%.

14. An aerodynamic toy of claim 2, 4 or 5, wherein at least one of said upper surface and lower surfaces of said airfoil having one or more cavities or slots.

15. An aerodynamic toy of claim 2, 4 or 5, wherein said airfoil having one or more holes forming a communicating surface between said upper surface and said lower surface.

16. An aerodynamic toy of claim 2, 4 or 5, wherein said lower surface of said airfoil having one or more cavities.

17. An aerodynamic toy of claim 7, wherein said airfoil having one or more cavities, slot, or holes.

18. An aerodynamic toy of claim 1, 2, 3, 4 or 5, wherein said airfoil having a cord line length of about 3 cm to about 30 cm, a maximum thickness of about 1 cm to about 7 cm, and a value of $C_o$ of about 2 cm to about 20 cm, as measured at an elongation of at least 50%.

19. An aerodynamic toy of claim 8 wherein at least one of said upper surface and lower surfaces of said airfoil having one or more cavities or slots.

20. An aerodynamic toy of claim 7, wherein said airfoil having a cord line length of about 3 cm to about 30 cm, a maximum thickness of about 1 cm to about 7 cm, and a value of $C_o$ of about 2 cm to about 20 cm, as measured at an elongation of at least 50%.

* * * * *